US007892254B2

(12) United States Patent
Klint et al.

(10) Patent No.: US 7,892,254 B2
(45) Date of Patent: Feb. 22, 2011

(54) EMBOLIZATION METHOD FOR ENDOVASCULAR OCCLUSION

(75) Inventors: Henrik S. Klint, Lyngby (DK); Arne Molgaard-Nielsen, Copenhagen Ø (DK); Erik E. Rasmussen, Slagelse (DK)

(73) Assignee: William Cook, Europe A/S, Bjaeverskov (DK)

( * ) Notice: Subject to any disclaimer, the term of this patent is extended or adjusted under 35 U.S.C. 154(b) by 287 days.

(21) Appl. No.: 10/813,783

(22) Filed: Mar. 30, 2004

(65) Prior Publication Data

US 2004/0186491 A1 Sep. 23, 2004

Related U.S. Application Data

(62) Division of application No. 08/923,061, filed on Sep. 3, 1997, now Pat. No. 6,776,788.

(60) Provisional application No. 60/040,737, filed on Mar. 12, 1997.

(30) Foreign Application Priority Data

Sep. 3, 1996 (DK) ........................................ 938/96

(51) Int. Cl.
*A61B 17/08* (2006.01)
*A61M 29/00* (2006.01)
*A61F 2/02* (2006.01)
(52) U.S. Cl. ...................... 606/213; 606/200; 623/23.72
(58) Field of Classification Search ................. 606/200, 606/153, 191, 213; 623/1.1, 1.11, 23.72; 128/898
See application file for complete search history.

(56) References Cited

U.S. PATENT DOCUMENTS 4,994,069 A 2/1991 Ritchart et al.
(Continued)

FOREIGN PATENT DOCUMENTS

DE 3203410 11/1982
(Continued)

OTHER PUBLICATIONS

"Detachable Embolization Coils," Cook Incorporated 1996.
"Tornado Embolization Microcoils™," Cook Incorporated 1995.

*Primary Examiner*—Julian W Woo
(74) *Attorney, Agent, or Firm*—Brinks Hofer Gilson & Lione

(57) ABSTRACT

An embolization device for positioning in a blood vessel comprises an elongated wire body (1) which in its unloaded condition has a predetermined shape and has an elongated shape with a substantially straight center line during its insertion through a catheter (18) to a placement site in the blood vessel and after its release from the catheter assumes a complexly curved shape which depends on the predetermined shape and on the blood vessel impact on the wire body. In its predetermined shape the wire body has at least one section (4) located between its front and back ends in which the center line has substantially no curvature or such a small curvature that along a length of at least 20 mm it follows a helix-free path. The front end section (2, 2", 2''') of the wire body is adapted to be frictionally locked to the vessel wall when discharged from the catheter, before said helix-free section (4) has been discharged from the catheter. When the helix-free section (4) is discharged it will bend sideways and seek towards the middle of the vessel lumen and continue towards the opposite vessel wall where it is frictionally locked. At continued pushing out many such vessel-crossing wire portions (20) occur, which provides efficient occlusion of the vessel. One advantage of the embolization device is that it may be used to occlude blood vessel areas. Accordingly, a method is described for occluding a blood vessel area using the wire body (1).

22 Claims, 3 Drawing Sheets

U.S. PATENT DOCUMENTS

| | | | |
|---|---|---|---|
| 5,054,501 | A | 10/1991 | Chuttani et al. |
| 5,122,136 | A | 6/1992 | Guglielmi et al. |
| 5,122,154 | A | 6/1992 | Rhodes |
| 5,167,624 | A | 12/1992 | Butler et al. |
| 5,217,484 | A | 6/1993 | Marks |
| 5,256,146 | A | 10/1993 | Ensminger et al. |
| 5,350,397 | A * | 9/1994 | Palermo et al. ............ 606/200 |
| 5,540,701 | A | 7/1996 | Sharkey et al. |
| 5,669,931 | A | 9/1997 | Kupiecki et al. |
| 5,690,671 | A * | 11/1997 | McGurk et al. ............ 606/200 |
| 5,797,953 | A * | 8/1998 | Tekulve ............ 606/200 |
| 5,895,398 | A | 4/1999 | Wensel et al. |

FOREIGN PATENT DOCUMENTS

| | | |
|---|---|---|
| DE | 29518932 | 1/1996 |
| EP | 0121447 | 10/1984 |
| EP | 0717969 | 6/1996 |
| EP | 0720838 | 7/1996 |
| EP | 0734697 | 10/1996 |
| RU | 1777842 | 11/1992 |
| WO | 9406502 | 3/1994 |
| WO | 9406503 | 3/1994 |
| WO | 9407560 | 4/1994 |
| WO | 9411051 | 5/1994 |
| WO | 9525480 | 9/1995 |
| WO | 9600104 | 1/1996 |
| WO | 9618343 | 6/1996 |

* cited by examiner

EMBOLIZATION METHOD FOR ENDOVASCULAR OCCLUSION

This application is a continuation of application Ser. No. 08/923,061, filed Sep. 3, 1997, now U.S. Pat. No. 6,776,788 hereby incorporated herein by reference, which claims the benefit of provisional Application No. 60/040,737, filed Mar. 12, 1997, hereby also incorporated herein by reference, which claims the benefit of Danish Patent Application No. 938/96, filed Sep. 3, 1996, hereby also incorporated herein by reference.

TECHNICAL FIELD

The present invention relates to a method for endovascular occlusion, comprising advancing a catheter percutaneously until a catheter is located at an area to be occluded, providing a wire body with a section connecting the front and the back of the wire body where the section is substantially straight in an unloaded condition and a length of the section is larger than a diameter of the area to be occluded, inserting the wire body into the catheter in which the catheter thereby loads the wire body into a substantially straight condition, pushing the wire body forward through the catheter until the front of the wire body is pushed out of the catheter, abutting a wall portion of the area to be occluded with the front of the wire body such that the wire body frictionally locks against the wall portion, and continuing to push the wire body out of the catheter thus curving the section of the wire body toward another wall portion, where the section of the wire body frictionally locks against the other wall portion of the area to be occluded thus forming a portion of the wire body that crosses the area and is frictionally locked to the wall portions.

BACKGROUND OF THE INVENTION

Embolization devices in the form of coils where the wire body is formed by a thread extending helically around the center line of the wire body are well-known within radiology, where embolization coils are used for a number of different purposes all with the common feature that it is desired to limit or stop the free flow of blood in an area of a blood vessel. As examples of endovascular fields of application for embolization devices for percutaneous, transluminal insertion using minimally invasive techniques can be mentioned occlusion of an aneurism to prevent rupture of the vessel wall with resulting bleeding. Aneurisms may occur anywhere in the vascular system, but particularly cerebral and abdominal aneurisms require treatment to avoid life-threatening conditions. Another application is occlusion of arteriovenous malformations (AVM), where short-circuiting of arteries and veins looking like skeins of wool may occur, or occlusion of arteriovenous shunts or fistulas, which are major short-circuits between the artery side and the vein side in the vascular system with resulting heavy undesired blood flow. A fourth example of an application is blocking of the blood flow to a tumor, and a fifth, closure of traumatically conditioned blood flows owing to incised wounds or other bodily injuries or gastrointestinal bleeding.

Since embolization devices can be used in many different places in the vascular system and in vessels with very differing sizes, many different coils have been specially designed with various basic designs of the predetermined shape, and each basic design is usually made in a number of different sizes. To treat emergency patients, radiologists today have to stock a large number of different coils, and in the endovascular repair normally many coils are used which are inserted individually and are placed in a pile at the site of placement to be occluded. Considerable expertise is required to select the correct coil sizes for the relevant application, and the risk of unintended migration of a coil to other vessel sites owing to insufficient fitting within the vessel cannot be disregarded.

Conventionally, the predetermined shape of the embolization devices is made so that the wire body is helical with a helix diameter of the same size or slightly larger than the relevant vessel lumen, so that the wound wire body exerts an abutment pressure against the vessel wall. If the helix diameter is too large, the pressure against the vessel wall may become injuriously high, and if it is too small, the wire body can easily be released and drift away. Embolization coils with a regular helical shape or irregular coil shape are known from, for example, U.S. Pat. No. 4,994,069, U.S. Pat. No. 5,122,136, WO94/11051 and WO94/11051; SU-1777842-A1 discloses a coil with a single helix, WO95/25480 describes a spiral coil, DE-295 18 932-U1 a spherical coil, and WO96/18343 and U.S. Pat. No. 4,994,069 coils with a random matrix shape.

Before insertion of the embolization device, a catheter is placed transluminally in the vascular system having its distal catheter end at the site of placement, whereupon a guidewire mounted with the embolization device is pushed in through the catheter. When the wire body leaves the distal end of the catheter, it seeks to assume the predetermined shape. If the size and shape of the device are deemed suitable for the vessel geometry at the site of placement, the wire body is disconnected from the guidewire. A number of applicable types of coupling means in the back end of the guidewire with associated corresponding part on the guidewire are known, see for example EP-A-720 838 disclosing a screw thread, U.S. Pat. No. 5,217,484 disclosing a prehensile claw, WO94/06503 disclosing a pin connection, WO94/06502 disclosing a clamp connection, WO96/00104 disclosing a conical thread connection and EP-A 717 969 disclosing an inflatable holder.

SUMMARY OF THE INVENTION

The object of the present invention is to provide an embolization device which is applicable for a number of different vessel geometries and sizes and which at its placement in the vessel assumes a complexly curved shape which provides effective occlusion by means of the wire body itself. It is also desirable to achieve the occlusion with a smaller number of devices than is possible in the known art in order thus to reduce the risk of travel of a device away from the site of placement and to reduce the time spent on performing the occlusion.

In view of this the embolization device according to the invention is characterized in that the wire body in its predetermined shape has at least one section located between its front and back ends in which the center line has substantially no curvature or such a small curvature that along a length of at least 20 mm it follows a helix-free path, and that the front end section of the wire body is adapted to be frictionally locked to the vessel wall at its discharge from the catheter, before said helix-free section has been discharged from the catheter.

The distal end of the catheter is usually located immediately at or at a short distance from the site of placement when the front end section of the wire body is discharged from the catheter. During the discharging, the end section will approach and abut the vessel wall. At the continued discharge, the end section will arrange itself along the vessel wall over a length that causes the end section to frictionally lock with the vessel wall. Frictional locking in the present context means that the frictional forces between the distal end section and the vessel wall reach a magnitude at which the column loading from the free end of the wire body located between the catheter opening and the closest point of abutment with the vessel wall is unable to move the end section in relation to the vessel wall. As the helix-free section has a length of at least 20 mm, at least part of the section will still be inside the catheter when the end section becomes frictionally locked. At the subsequent release of the helix-free section, the free portion thereof will bend sideways away from the closest point of abutment with the vessel wall and seek towards an opposite area of the vessel wall, as seen in relation to the closest point of abutment, where a frictional locking will also occur. Then discharge of a further portion of the helix-free section of the catheter will lead to renewed bending of the wire body in a new direction, etc. The length of the helix-free section can be adapted to the vessel geometry at the site of placement to be occluded, a longer helix-free section for the same vessel geometry making the embolization device arrange itself with more portions of the wire across the vessel lumen, thereby making the occlusion denser, and a shorter helix-free section producing a more open occlusion, should this be desired.

The embolization device provides the considerable advantage that the helix-free section itself automatically adapts to the vessel geometry in question, and is fastened securely to it without any risk of unintended release from the site of placement. The various fields of application of the embolization device display different specific problems, for example that the wire body should only exert a relatively limited pressure on the vessel wall at placement in an aneurism where the vessel wall may be in danger of rupturing, but has to exert a substantially larger pressure on the vessel wall at placement in a vessel to be occluded for blocking of the blood supply to a tumor or an AVM, where the vessel wall is strong and the certainty against release of the wire body has to be high. All these different desired properties of the device can be taken into consideration by designing the wire body with a rigidity adapted to the desired application, a greater rigidity providing a heavier abutment pressure against the vessel wall.

The device according to the invention has the further advantage that the cavity in the vessel is crossed by the wire body suitably many times in different directions. The wire body has an own rigidity effectively counteracting recanalization at the site of occlusion, and the crossing wire portions also abut the vessel wall at each end of the crossing portions, which also contributes to the long-term stability of the occlusion. The placement is furthermore conducted in such an orderly manner that the risk of knotting or locking filtration of the wire body is extremely low. This provides the advantage that if desired the wire body can always be repositioned in the catheter by retraction of the proximal end of the member.

Preferably at its back end the wire body has a coupling means so that at insertion and placement the embolization device is mounted on the guidewire, thus rendering it possible directly to reposition the device in the catheter in case of problems in connection with the occlusion. It is also possible to manufacture the embolization device without any coupling means and to push out the device from the catheter by means of a stylet-shaped pusher.

In some applications the front end section may constitute a substantially rectilinear extension of the helix-free section, and at its distal extreme end the end section may be provided with a guide means, which may, for example, be umbrella-shaped. Alternatively the device in a preferred embodiment may be formed so that the helix-free section of the wire body extends to the front end section, which is curved at its front end, the center line of the section here turning at least 90°, preferably from 120° to 320°, in relation to the course of the center line in the helix-free section when the wire body assumes its predetermined shape.

Firstly, the curved end section gives the wire body a soft and flexible front end with an extremely low risk of injuring the vessel wall when the front end meets it. This embodiment is therefore suitable for embolization of aneurisms. If, at the time of placement, the catheter end is positioned so that the pushing-out direction of the wire body is at right angles to the vessel wall in the aneurism, the vessel wall is touched by the curved front end which, owing to its curvature, is resiliently deformed without applying any risky pressure to the vessel wall, and at the same time the wire body is maneuvered to the side to follow the vessel wall. If the pushing-out direction forms an oblique angle with the vessel wall, the curved end section results in a turn of the wire body so as to follow the curvature of the vessel wall.

Secondly the curved end section is an integral part of the wire body, and transverse forces acting on the end section when it meets the vessel wall may therefore via the end section be partially transmitted to the section of the wire body located further behind, so that it is maneuvered to fit with the shape of the vessel wall before it has been advanced all the way to the vessel wall. For application in aneurisms, the center line in the front end of the wire body preferably turns through an angle ranging from 120° to 320°. Keeping the angle below 320° prevents the end section in the predetermined shape from forming a full helical line which may, after placement in the aneurism, exert a greater pressure against the vessel wall than the pressure of the helix-free section, which is determined by the rigidity of the wire, as mentioned above. The angle of at least 120° provides great certainty that the end section will nestle up along the vessel wall in the advantageously atraumatical manner.

For applications in aneurisms, the embolization device may further advantageously be formed so that the back end section of the wire body with the coupling means is curved, the center line of the end section turning at least 120°, and preferably from 140° to 340° when the wire body assumes it predetermined shape. When the embolization device has been placed in the aneurism in the complexly curved shape, the curved back end section causes the coupling means to lie protected inside the cavity of the aneurism, surrounded by the wire portions crossing the cavity. With this location, the coupling means is prevented from sticking out through the access opening to the aneurism and from abutting the vessel wall of the aneurism. An angle smaller than 120° or larger than 340° in some cases entails the risk that the coupling means sticks out.

When the embolization device is intended for placement at sites where the vessel has a relatively large lumen and a suitably strong wall, for example in vessels with AVM, shunts or fistulas, the front end section of the wire body is preferably curved and forms several helices, suitably in the form of a spiral with a decreasing helix diameter towards the front end when the wire body assumes its predetermined shape. When the front end section is discharged through the catheter opening, it assumes the helical shape immediately outside the catheter opening and can thereby be frictionally locked to the vessel wall in a very well-defined position in the vessel. The catheter can then be slightly retracted so that the helix-free section has a suitable free length between the end section and the catheter opening, whereupon the whole wire body can be pushed out of the catheter so that it automatically adapts to the vessel geometry in the manner described above. If the distal helices have a small diameter, they will be placed centrally in the lumen of the vessel and here prevent the outward curving wire body portions from being pressed centrally through and out on the other side of the already placed distal end section. Thus, in addition to an accurate positioning, the embodiment also renders it possible to achieve a compactly placed device that only extends over a short vessel length.

In a particularly simple embodiment the helix-free section extends from the front to the back end sections. Thus, the whole wire body can have homogeneous properties except in the two end sections. Such an embolization device has a wide field of application. For special applications, the device may alternatively be designed so that between the front and the back end sections there are several helix-free sections with intermediate sections which may be helical and/or may produce breakpoints in the curvature of the wire body when it assumes its predetermined shape. With a single embolization device of this design it is possible to occlude two or more mutually separated places in a vessel, for example on both sides of a fistula. When the front section of the wire body is positioned at the first site in the vessel, and the front helix-free section(s) is/are placed, the catheter can be retracted in the vessel to a position at the desired second site of occlusion, whereupon an intermediate section of the wire body is placed and frictionally locked to the vessel, and finally the remainder of the device is placed. The sections of the wire body placed at individual sites of occlusion are mutually connected via a portion of the wire body, which prevents travel of the embolization device away from one occlusion site. Furthermore the insertion procedures for provision of two separate occlusions are considerably facilitated.

The wire body can be formed in different ways. One possibility is to use a single solid thread of wire which is bent in the end sections to the desired predetermined shape. In the front end section the wire may have a smaller diameter and be wound helically around the center line of the section to increase the flexibility of the wire body front end. Another possibility is to construct the wire body from several thin threads which are laid, woven or braided together into a body of a larger diameter than the thin threads. From the manufacture of ropes or wires it is known that the laying, weaving or braiding can be effected in a pattern that imparts resilient properties to the resulting wire body. Owing to the extremely small outer diameter of the threads, this method of manufacture is costly, however. A third and preferred possibility is to form the wire body from a thread that extends helically around the center line of the wire body. This design involves several advantages. From the manufacture of conventional embolization coils it is well-known to wind a thin thread around a mandrel in order to provide an embolization coil, and in terms of manufacturing it is an advantage to manufacture the wire body by this well-tried technique. For a specific desired rigidity (or rather flexibility) of the wire body, the wire body may be given a rather large diameter with a helically wound thread, which gives the radiologist a better possibility of seeing the wire body during its positioning in the vessel, because the larger diameter makes the wire body more radiopaque.

In a preferred embodiment, in the helix-free section the wire body has a spring constant which, measured on a 50 mm long portion of the wire body, is of at least $c=P/e \geq 0.0008$ N/mm, P being an axially acting applied force measured in N, and e being the change in length measured in mm, preferably of $0.0015$ N/mm $\leq c \leq 0.08$ N/mm, suitably in the interval of $0.008$ N/mm $\leq c \leq 0.2$ N/mm. The preferred spring constant depends on the relevant application, on the method of insertion and on the intended pressure of the device against the vessel wall. If the spring constant becomes substantially lower than 0.0008 N/mm, the ability of the device to lock against the vessel wall will become poor. For application in aneurisms having a diameter of up to 6 mm, the spring constant preferably ranges from 0.0015 N/mm to 0.08 N/mm, and for applications where the vessel wall is stronger, the spring constant preferably ranges from 0.008 N/mm to 0.2 N/mm.

Accordingly, another object of the invention is to provide a method for endovascular occlusion of blood vessel areas. The method involves advancing a catheter percutaneously to an area to be occluded. A wire body is provided with a section that is substantially straight in an unloaded condition and in which the length of the section is larger than a diameter of the area to be occluded. The wire body is inserted into the catheter, thus causing the wire body to be loaded into a substantially straight condition. The wire body is then pushed forward through the catheter until the front of the wire body is pushed out of the catheter. As a result, the wire body abuts a wall portion of the area to be occluded, thereby frictionally locking the wire body against the wall portion. The pushing of the wire body is then continued, thereby causing the section of the wire body to curve toward another wall portion. As a result, the section of the wire body becomes frictionally locked against the other wall portion of the area to be occluded, thereby forming a portion of the wire body that crosses the area and is frictionally locked to both wall portions.

BRIEF DESCRIPTION OF THE DRAWING

Examples of embolization devices according to the invention will now be explained in further detail below with reference to the highly schematic drawing, in which.

DETAILED DESCRIPTION

Figure 1:
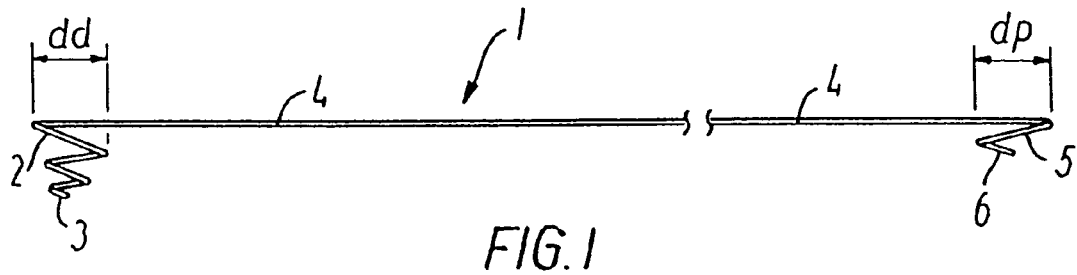
FIG. 1 shows a side view of a first embodiment of the device according to the invention in its predetermined unloaded shape.

FIG. 1 shows a wire body generally designated 1 in an embolization device shown in the predetermined unloaded shape. The wire body has a distal or front end section 2 formed as a spiral with a decreasing helix diameter in the direction of the front end 3, and a helix-free section 4 connecting the end section 2 with a proximal or back end section 5, the center line of which turns through an angle of about 340° compared with the substantially rectilinear course of the center line in the section 4. The back end of the wire body has a coupling means 6 which may, for example, be formed as explained in connection with FIG. 12. The dimensions of the wire body depend on the vessel geometry at the site to be occluded.

The largest helix diameter dd in the end section 2 typically corresponds to the diameter of the vessel lumen and may, for example, be of the same size or slightly larger than this lumen. The smallest helix diameter can be half or slightly over half of the largest diameter. The diameter dp in the helical portion of the back end section 5 may be comparable with or smaller than the largest helical diameter in the front end section 2. The helix-free section 4 has a length substantially larger than the diameter of the vessel lumen, for example at least six times the size, which may typically provide at least four wire portions crossing the vessel lumen. The front end section 2 may, for example, have a largest external diameter in the range from 2 to 13 mm. The helix-free section 4 may, for example, have a length in the range from 30 to 1000 mm, and suitably in the range from 30 to 300 mm, if no measures have been taken to reduce the friction between the wire body and the inner surface of the catheter. Finally the back end section 5 may have a largest external diameter in the range from 2 to 13 mm, suitably from 4 to 8 mm. If the vessel has a lumen of 2 mm at the site of occlusion, the end sections 2 and 5 may be pre-shaped with an external diameter of about 2 mm, and the section 4 may have a length of at least 20 mm, which renders it possible to have more than 10 wire passages across the vessel lumen. If the vessel has a lumen of 6 mm, the end section 2 may have a largest external diameter of about 6 mm, the end section 5 a diameter of about 5 mm and the section 4 a length of at least 50 mm. If a more dense occlusion is desired, the section 4 may be given greater length.

The wire body 1 may, for example, be manufactured by helical winding of a thread around a mandrel. The thread may, for example, be of platinum, palladium silver, gold, nitinol, stainless steel, alloys of these materials or of a springy plastic, such as modified butadiene. Platinum is the preferred material owing to its great radiopacity. The thread diameter is adapted to the diameter of the wire body and the desired rigidity of the wire body and may, for example, in the range from 0.02 to 0.2 mm, preferably from 0.04 to 0.1 mm. At superselective applications, such as intracranial or renal occlusion, occlusion in the liver or in vessels at joints or bones, the thread may advantageously have a diameter in the range from 0.35 to 0.45 mm. Along the main part of the length of the wire body the thread may be spun at a pitch corresponding to the thread thickness so that the windings touch each other. This increases the compressive strength of the wire body, which is a particular advantage if the wire body in its extended shape is very long so that noticeable friction has to be overcome at its advancement through the catheter. For the same thread thickness the rigidity of the wire body decreases with increasing diameters of the body. The wire body may typically have an external diameter in the range from 0.0254 mm (10 mils) to 1.016 mm (40 mils), preferably from 0.0254 mm to 0.457 mm (10-18 mils). If the site of occlusion has a very small lumen, the diameter may be chosen to be smaller than 0.0254 mm.

After spinning of a straight coil piece, a piece thereof is cut off in a length corresponding to the extended length of the wire body. Then the end sections 2, 5 can be deformed around a mandrel to the desired shape. Finally, the wire body can be heat-treated in an oven in a well-known manner. If the section 4 is longer than the length of the oven chamber, it is necessary to wind the whole wire body 1 together into a coil size capable of being accommodated inside the oven. After the heat treatment of such a body, the section 4 may retain the wound shape in which the diameter of the windings is much larger than the diameter of the end sections 2, 5. When the section 4 in the present connection is characterized as being helix-free this means that the section has no helices of a diameter comparable with the vessel lumen at the site of placement. Thus, for manufacturing reasons the helix-free section 4 may have been given a winding-forming curved shape, the winding diameter being at least 10-25 times larger than the vessel lumen at the site of placement.

In the following description of other embodiments the same reference numerals will be used for components of the same sort as in the above embodiment for the sake of simplicity.

Figure 2:
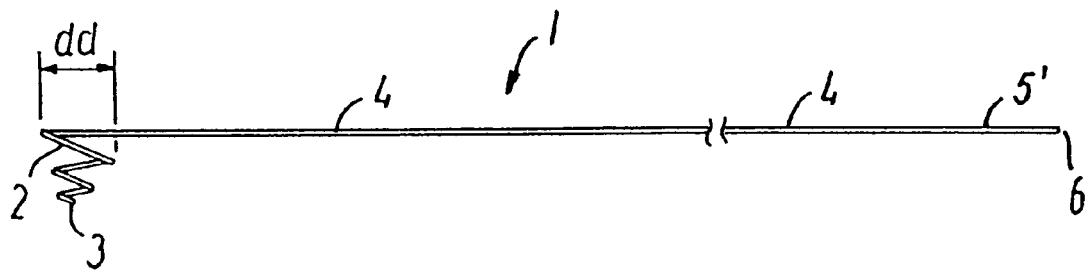
FIGS. 2 and 3 show a second and a third embodiment, also in their predetermined, unloaded shapes.

The embodiment shown in FIG. 2 also comprises a wire body 1 with a front end section 2 being spiral-shaped, and with a helix-free section 4, but the end section 5' is here formed as an approximately rectilinear extension of the section 4. The embodiment is simpler to manufacture because the end section 5' does not have to be pre-shaped in a curved shape. This is possible if the coupling means 6 is of a type that cannot damage the vessel wall by direct abutment with it, for example if the coupling means is spherical for engagement with a holder at the end of the guidewire, or if the back end of the wire body 1 is gripped by an inflatable member at the end of the guidewire.

Figure 3:
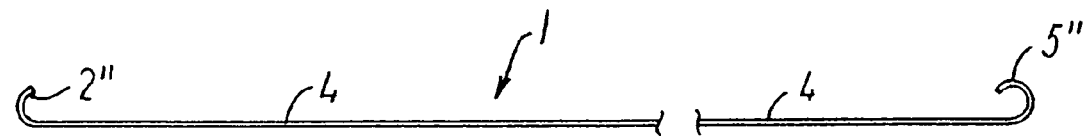

The embodiment shown in FIG. 3 is particularly applicable for occlusion of aneurisms. The embolization device here comprises a wire body 1 with a helix-free middle section 4, a front end section 2" and a back end section 5". The center axis of the front end section 2" turns through an angle of about 130°, which ensures that the front end of the wire body cannot meet the vessel wall directly when advanced into the aneurism. The center axis of the back end section 5" turns through an angle of about 210°, which ensures that the coupling means does not touch the vessel wall when the device is fully placed in the aneurism.

Figure 14:
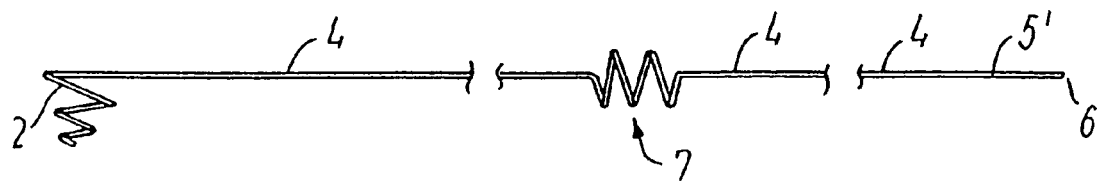
FIG. 14 is a side view of an embodiment having several helix-free sections between its end sections with intermediate helical sections shown in the predetermined unloaded shape.

FIG. 14 shows an embodiment suitable for occlusion at two or more mutually separate sites in a vessel. The device comprises a wire body 1 having at least two helix-free sections 4, a front end section 2 formed similarly to those in FIGS. 1 and 2, and a back end section 5' formed as in FIG. 2. The helix-free sections are mutually connected via intermediate sections 7 which in the predetermined shape have helical courses with an external diameter in the windings corresponding to the lumen of the vessel. To achieve a suitable occlusion at the site of placement, the helix-free section(s) 4 preferably has/have an aggregate length of at least 90 mm, suitably a length in the range from 100 to 700 mm.

Figure 12:
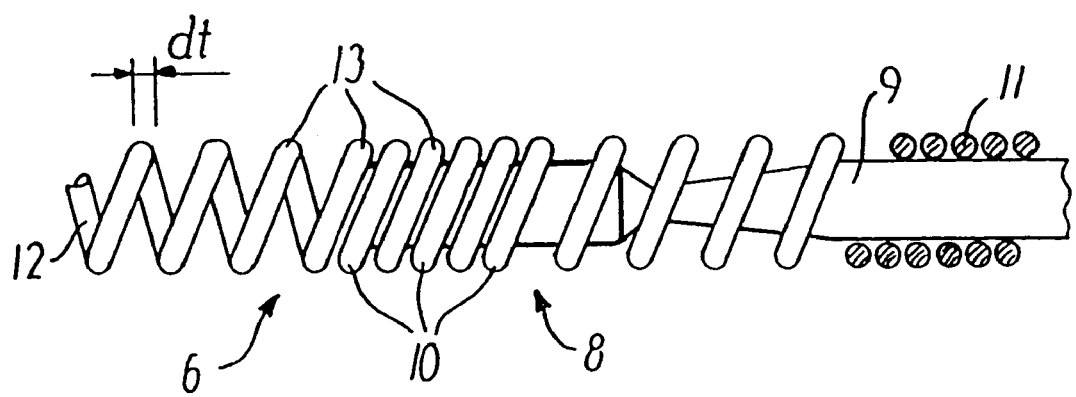
FIG. 12 is an example of a coupling means in the back end of the wire body.

FIG. 12 shows an example of a coupling means 6 intended for screwing into a thread 8 at the distal end of a guidewire 9. The thread on the guidewire has been provided by fixing the windings 10 in a protective coil 11 at a pitch slightly larger than the diameter dt of the thread 12 of the wire body. The coupling means 6 has been provided by axially pulling out the windings 13 of the back end of the wire body until they display a pitch corresponding to the pitch in the thread on the guidewire. The other known types of coupling means are also applicable. If it is not necessary to be able to reposition the embolization device in the catheter, it can, instead of being mounted on a guidewire, be discharged from the catheter by means of a stylet-shaped pusher not connected with the wire body, but only pushing it forwards through the catheter.

Figure 13:
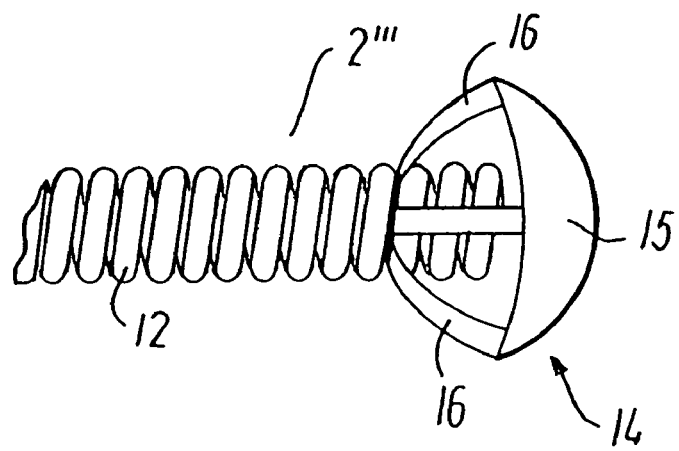
FIG. 13 is a side view of an embodiment of the front end section of the wire body, the end section being straight and carrying a separate guide means.

The different above curvatures in the front section of the wire body constitute a kind of guide means which is an integral part of the wire body and prevents the front end of the wire body from damaging the vessel wall when it is pushed out from the catheter. The front end section 2''' may alternatively have a center axis being a rectilinear extension of the center axis of the section 4, and in that case the front end of the wire body may be provided with a separate guide means 14, which may, for example, have the design shown in FIG. 13.

The guide means 14 is umbrella-like with a front dish-shaped screen 15 of a thin and springy material, such as nitinol, platinum or plastics. Via several thin struts 16 the screen 15 is placed in engagement with the end section of the wire body so that the screen lies protectively in front of the end of the wire body. The screen has a relatively large radius of curvature, preferably of at least five times the external diameter of the wire body. This means that firstly the screen distributes the abutment pressure of the front end on the vessel wall over a suitably large areal, and secondly it makes the front end turn to the side at continued pushing out of the wire body from the catheter so that the front end section nestles along the vessel wall and is frictionally locked to it in the manner described above. As the struts 16 are thin and the screen is located in front of the end of the wire body the screen will lie folded together in front of the wire body when it is advanced through the catheter, which renders possible advancement through a catheter with the same internal lumen as the catheters used for the above embodiments.

Clearly, details of the above embodiments can be combined for the provision of new embodiments, and at least the front end section 2 can also have a helical shape with windings of a substantially constant external diameter. The intermediate section 7 shown in FIG. 14 may alternatively have a spiral shape.

Figure 4:
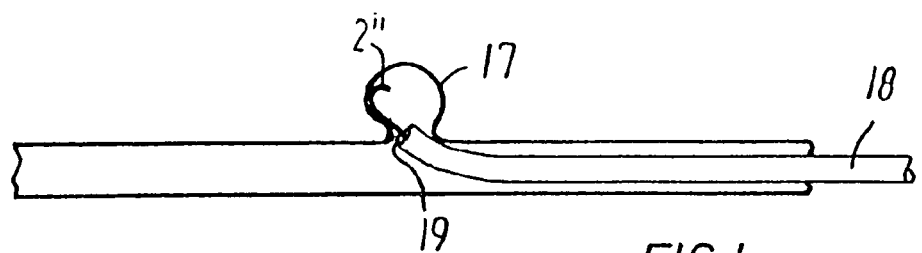
FIGS. 4-7 are illustrations of placement in an aneurism of the embodiment shown in FIG. 3, FIGS. 8-10 illustrate placement in a vessel of the embodiment shown in FIG. 1.
Figure 5:
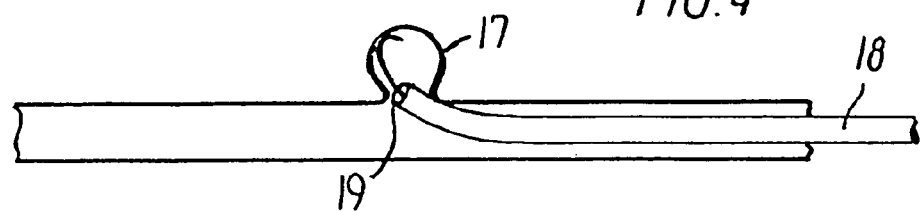
Figure 6:
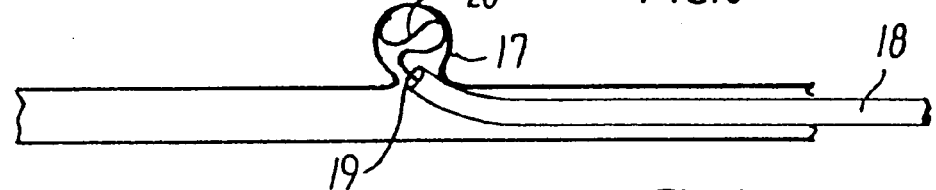
Figure 7:
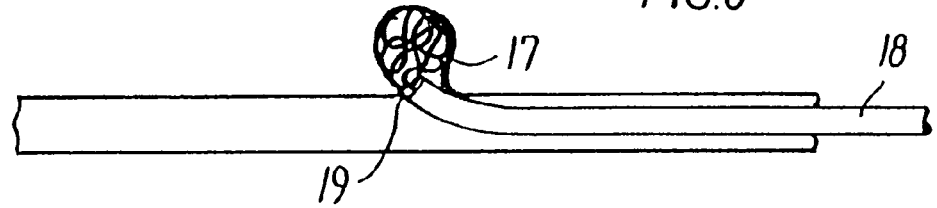

Now placement of the embolization device in an aneurism 17 will be described in detail with reference to FIGS. 4-7. An introducer catheter 18 is advanced percutaneously and transluminally in a well-known manner along a suitable path until the distal opening 19 of the catheter is located in the neck of the aneurism as shown in FIG. 4. Then a guidewire mounted with the embolization device is inserted into the catheter and pushed forwards until the front end section 2" meets the vessel wall, whereupon the end section at continued pushing out is automatically guided by the curvature of the end section towards abutment with the vessel wall in a frictionally locking manner. FIG. 5 shows the situation where the frictional locking has been established. At the continued pushing out, the helix-free section 4 in front of the catheter opening 19 curves into a direction towards the middle of the aneurism and further towards the opposite vessel wall where frictional locking also takes place as shown in FIG. 6. A portion 20 of the section 4 thus crosses the aneurism and at either end is locked to the vessel wall. At the continued pushing out this sequence repeats itself, the section 4 after each frictional locking to the vessel wall again seeking towards the middle of the aneurism and finding another abutment place on the opposite vessel wall. FIG. 7 shows the situation immediately before the whole wire body has been placed, and it can be seen that the helix-free section has assumed a complexly curved shape in which the curvatures of the section vary continuously and without breakpoints that might cause a local overload of the vessel wall, and that the resulting course of the section 4 causes the aneurism to be crossed by many wire portions.

Figure 8:
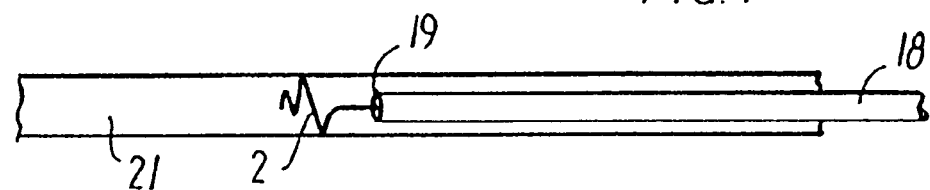
Figure 9:
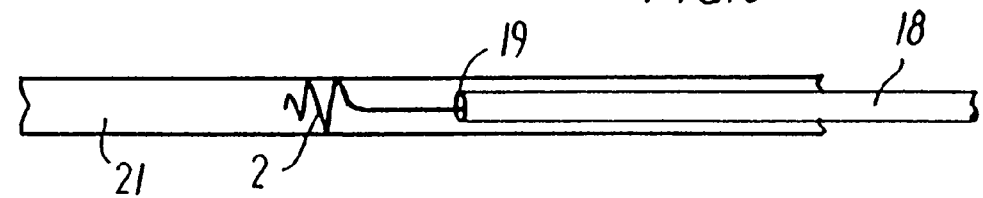
Figure 10:
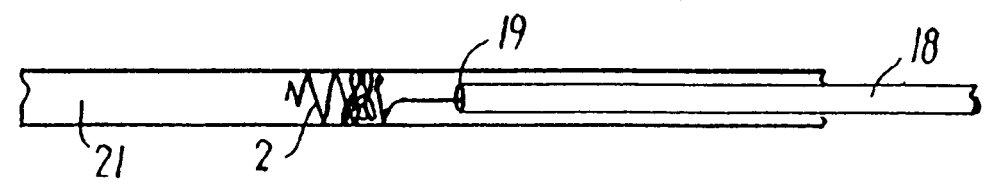
Figure 11:
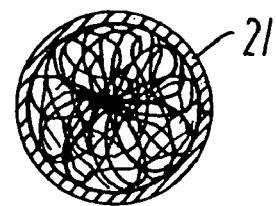
FIG. 11 is a cross-sectional view of the vessel of FIG. 10 seen in a direction towards the site of occlusion.

FIGS. 8-10 illustrate the placement of an embolization device in a vessel 21 with a healthy vessel wall, but where it is desired to occlude the vessel itself. First the catheter 18 is introduced as mentioned above, and then the embolization device is advanced, and the front end section 2 is pushed out through the catheter opening 19 and assumes its predetermined shape, the end section lying frictionally locked to the vessel wall as shown in FIG. 8. Then the catheter is retracted slightly to the position shown in FIG. 9, where the section 4 has a free length between the section 2 and the catheter opening so that the column loading in the wire body makes the released part of the section 4 curve to the side at the continued pushing out. The section 4 will then in a similar manner as that described above meet the vessel wall and be frictionally locked to it, whereupon it will seek towards the vessel center and onwards for frictional locking on an opposite area of the vessel wall, and so forth until the whole wire body has been placed. FIG. 10 shows the partially occluded vessel before conclusion of the placement, and FIG. 11 shows the vessel after concluded placement of an embolization device having a section 4 of large length. It is directly seen that the many vessel-crossing wire portions produce an extremely efficient occlusion of the vessel, particularly at its center, where prior-art embolization coils have not been able to produce a sufficiently efficient occlusion to be able to avoid recanalization with any suitable degree of certainty.

Because the section 4 places itself across the vessel to be occluded, the occlusion can be performed solely by means of the wire body. Thus there is no need to use the formerly known occlusion hairs of silk or dacron to occlude the vessel center. This means that the embolization device according to the invention, when it is free of occlusion hairs, can be inserted through a catheter with advantageously smaller inner lumen than the known embolization coils with hairs because no space is required inside the catheter for the hairs. As these hairs also generate an unfortunate, high friction between the coil and the inner surface of the catheter, the device according to the invention is easier to advance through the catheter. This can be utilized to place wire members of a greater length and/or of lower rigidity. If a further advantageous reduction of the friction is desired, the inner surface of the catheter or possibly the wire body itself may be coated with a friction-reducing coating, such as a PTFE coating or a hydrophilic coating. Naturally it is possible within the scope of the invention to provide the wire body with occlusion hairs, but it is not preferred for the above reasons.

A number of experiments have been carried out to find suitable rigidities of section 4 of the wire body so that it obtains the desired vessel-wall seeking rigidity without becoming so stiff that the outward pressure on the vessel wall becomes too high. The experiments were carried out with helically wound platinum threads for different thread diameters d and for different external diameters D of the wire body, i.e., external diameters of the helical windings. For each geometrical set five experiments were carried out in which a coil piece 50 mm long was clamped in holders in a stretching apparatus whereupon the holders were pulled apart to an extension e=10 mm, and the tensile force P required for this was measured. On this basis the spring constant c=P/e was calculated. The result of this is reproduced in the below table 1.

TABLE 1

| D in mils | d = 0.1 mm c in N/mm | d = 0.075 mm c in N/mm | d = 0.05 mm c in N/mm |
| --- | --- | --- | --- |
| 18 | 0.040 | 0.0093 | 0.0008 |
| 16 | 0.046 | 0.012 | 0.0009 |
| 15 | 0.059 | 0.015 | 0.0011 |
| 14 | 0.109 | 0.027 | 0.0020 |
| 12 | 0.202 | 0.033 | 0.0049 |
| 10 | 0.209 | 0.064 | 0.0049 |

The threads were subsequently pushed at right angles on to a plane surface to see whether the curving out took place in the desired manner. It turned out that the length of the free portion outside the catheter opening was important to the force exercisable on the plane surface. With a coil of D=14 mils and a thread thickness of d=0.075 mm and a projecting length of 5 mm a pressure of about 2 g could be measured, while with a projecting length of 20 mm no pressure could be recorded by the measuring apparatus used. When the spring constant is lower than 0.0008 N/mm, the coil no longer had a sufficient vessel wall seeking property.

It has been mentioned that section 4 may be completely straight in the predetermined shape. As the wire body 1 may be of great length and of a small diameter, it may be difficult at placement of the wire member on a plane surface to achieve a straight shape because there will be a certain friction against the supporting surface. If, instead, the wire body is suspended at the transition between the helix-free section and one of the end sections, the predetermined shape will appear clearly, and section 4 will hang down vertically without any curvature.

We claim:

1. A method for endovascular occlusion of a blood vessel area, comprising:
    advancing a catheter percutaneously and transluminally until a distal opening of said catheter is located at a blood vessel area to be occluded;
    providing a wire body comprising a front end, a back end, and a section connecting said front end and said back end, wherein said section is substantially straight in a predetermined unloaded shape, a length of said section being larger than a diameter of said blood vessel area;
    inserting said wire body into said catheter, said section of said wire body being substantially in said predetermined unloaded shape within said catheter;
    mechanically pushing said wire body forward through said catheter until said front end of said wire body is pushed out of said distal opening of said catheter;
    abutting a first wall portion of said blood vessel area with said front end of said wire body, thereby column loading said wire body and frictionally locking said front end against said first wall portion;
    continuing to mechanically push said wire body out of said distal opening of said catheter, thereby curving said section of said wire body toward a second wall portion of said blood vessel area, wherein said section of said wire body frictionally locks against said second wall portion of said blood vessel area when said section is column loaded between said first and second wall portions due to said wire body being mechanically pushed forward, thereby forming a portion of said wire body crossing said blood vessel area that is frictionally locked to said first wall portion and said second wall portion due to said column loading;
    physically separating said wire body from said catheter by pushing an entirety of said wire body out of said distal opening of said catheter;
    occluding blood flow in said blood vessel area to be occluded using said section of said wire body frictionally locked between said first and second wall portions, wherein said blood flow is occluded after said wire body is physically separated from said catheter and after said catheter is removed from said blood vessel area to be occluded; and
    forming a thrombus at a location of said wire body after said wire body is physically separated from said catheter and after said catheter is removed from said blood vessel area to be occluded.

2. The method according to claim 1, wherein said blood vessel area to be occluded is an aneurysm.

3. The method according to claim 2, wherein said front end of said wire body is curved in said predetermined unloaded shape at least 120° and said back end of said wire body is curved in said predetermined unloaded shape at least 120°.

4. The method according to claim 1, further comprising repeating said continuing step until said section of said wire body has assumed a complexly curved shape, whereby said section repeatedly crosses said blood vessel area and frictionally locks against wall portions of said blood vessel area when said section is column loaded between due to said wire body being mechanically pushed forward, said section thereby forming curvatures in said complexly curved shape, the curvatures varying continuously without breakpoints.

5. The method according to claim 1, wherein said blood vessel area to be occluded is a vessel lumen.

6. The method according to claim 5, further comprising retracting said catheter between said abutting and said continuing steps, wherein a free length of said section of said wire body extends between said front end of said wire body and said distal opening of said catheter, said continuing step thereby column loading said section as said wire body is mechanically pushed.

7. The method according to claim 6, further comprising repeating said continuing step until said section of said wire body has assumed a complexly curved shape, whereby said section repeatedly crosses said blood vessel area and frictionally locks against wall portions of said blood vessel area, said section thereby forming curvatures in said complexly curved shape which vary continuously without breakpoints.

8. The method according to claim 7, wherein said front end of said wire body in said predetermined unloaded shape is formed as a spiral with a decreasing helix diameter in the direction of said front end, a largest helix diameter corresponding generally to said diameter of said blood vessel area, and said length of said section of said wire body being at least six times said diameter of said blood vessel area.

9. The method according to claim 1, further comprising repeating said continuing step until said section of said wire body has assumed a complexly curved shape, whereby said section repeatedly crosses said blood vessel area and frictionally locks against wall portions of said blood vessel area, said section thereby forming curvatures in said complexly curved shape which vary continuously without breakpoints.

10. The method according to claim 1, wherein said front end of said wire body is curved in said predetermined unloaded shape at least 120°.

11. The method according to claim 1, wherein said back end of said wire body is curved in said predetermined unloaded shape between 140° and 340°.

12. The method according to claim 1, wherein said length of said section of said wire body is at least 20 mm.

13. The method according to claim 1, wherein said length of said section of said wire body is at least 90 mm.

14. The method according to claim 1, wherein said wire body is made of a thread extending helically around a center line of said wire body.

15. The method according to claim 1, wherein said wire body is further characterized by the absence of occlusion hairs, an inner lumen of said catheter being sized substantially to said wire body.

16. The method according to claim 15, wherein said wire body is made of a thread extending helically around a center line of said wire body.

17. The method according to claim 1, wherein said section of said wire body has a spring constant of $c=P/e$ measured on a 50 mm long portion of said wire body, P being an axially acting applied force measured in N and e being a change of length measured in mm, said spring constant being in the interval of $0.0015 \text{ N/mm} \leq c \leq 0.08 \text{ N/mm}$.

18. The method according to claim 1, wherein said front end of said wire body has a largest external diameter ranging from 2 to 13 mm, said length of said section of said wire body ranges from 30 and 300 mm, and said back end of said wire body has a largest external diameter ranging from 4 to 8 mm.

19. A method for endovascular occlusion of an aneurysm, comprising:
advancing a catheter percutaneously and transluminally until a distal opening of said catheter is located at an aneurysm to be occluded;
providing a wire body comprising a front end, a back end, and a section connecting said front end and said back end, said front end and said back end being curved and said section being substantially straight in a predetermined unloaded shape, a length of said section being larger than a diameter of said aneurysm, wherein said wire body is made of a thread extending helically around a center line of said wire body and said wire body is characterized by the absence of occlusion hairs, an inner lumen of said catheter being sized substantially to said wire body;
inserting said wire body into said catheter, said section of said wire body being substantially in said predetermined unloaded shape within said catheter;
mechanically pushing said wire body forward through said catheter until said front end of said wire body is pushed out of said distal opening of said catheter;
abutting a first wall portion of said aneurysm with said front end of said wire body, thereby column loading said wire body and frictionally locking said front end against said first wall portion;
continuing to mechanically push said wire body out of said distal opening of said catheter, thereby curving said section of said wire body toward a second wall portion of said aneurysm, wherein said section frictionally locks against said second wall portion when said section is column loaded between said first and second wall portions due to said wire body being mechanically pushed forward, thereby forming a portion of said wire body crossing said aneurysm and frictionally locked to said first wall portion and said second wall portion due to said column loading;
repeating said continuing step until said section of said wire body has assumed a complexly curved shape, whereby said section repeatedly crosses said aneurysm and frictionally locks against wall portions of said aneurysm when said section is column loaded between said wall portions due to said wire body being mechanically pushed forward, said section thereby forming curvatures in said complexly curved shape which vary continuously without breakpoints;
physically separating said wire body from said catheter by pushing an entirety of said wire body out of said distal opening of said catheter;
occluding blood flow in said aneurysm with said wire body having a complexly curved shape that is frictionally locked between said wall portions, wherein said blood flow is occluded after said wire body is physically separated from said catheter and after said catheter is removed from said aneurysm; and
forming a thrombus at a location of said wire body after said wire body is physically separated from said catheter and after said catheter is removed from said aneurysm.

20. A method for endovascular occlusion of a blood vessel lumen, comprising:
advancing a catheter percutaneously and transluminally until a distal opening of said catheter is located at a blood vessel lumen to be occluded;
providing a wire body comprising a front end, a back end, and a section connecting said front end and said back end, said front end in a predetermined unloaded shape being formed as a spiral with a decreasing helix diameter in the direction of said front end, a largest helix diameter corresponding to a diameter of said blood vessel lumen, and said section being substantially straight in said predetermined unloaded shape, a length of said section being at least six times said diameter of said blood vessel lumen, wherein said wire body is made of a thread extending helically around a center line of said wire body and said wire body is characterized by the absence of occlusion hairs, an inner lumen of said catheter being sized substantially to said wire body;
inserting said wire body into a proximal end of said catheter, said catheter thereby loading said wire body into a substantially straight condition;
mechanically pushing said wire body forward through said catheter until said front end of said wire body is pushed out of said distal opening of said catheter;
abutting a first wall portion of said blood vessel lumen with said front end of said wire body, thereby frictionally locking said front end against said first wall portion;
retracting said catheter to create a free length of said section of said wire body extending between said front end of said wire body and said distal opening of said catheter;
continuing to mechanically push said wire body out of said distal opening of said catheter thereby column loading said section as said wire body is mechanically pushed and curving said section of said wire body toward a second wall portion of said blood vessel lumen, wherein said section frictionally locks against said second wall portion due to said column loading of said section, thereby forming a portion of said wire body crossing said blood vessel lumen and frictionally locked to said first wall portion and said second wall portion;
repeating said continuing step until said section of said wire body has assumed a complexly curved shape, whereby said section repeatedly crosses said blood vessel lumen and frictionally locks against wall portions of said blood vessel lumen due to said column loading of said section, said section thereby forming curvatures in said complexly curved shape which vary continuously without breakpoints;
physically separating said wire body from said catheter by pushing an entirety of said wire body out of said distal opening of said catheter;
occluding blood flow in said blood vessel lumen to be occluded using said wire body having a complexly curved shape that is frictionally locked between said wall portions, wherein said blood flow is occluded after said wire body is physically separated from said catheter and after said catheter is removed from said blood vessel lumen to be occluded; and
forming a thrombus at a location of said wire body after said wire body is physically separated from said catheter and after said catheter is removed from said blood vessel lumen to be occluded.

21. The method according to claim 1, wherein said steps of mechanically pushing said wire body comprises pushing on a guidewire coupled to said back end of said wire body.

22. The method according to claim 1, wherein said steps of mechanically pushing said wire body comprises pushing on a stylet abutting said back end of said wire body, said stylet being unconnected to said wire body.

* * * * *

UNITED STATES PATENT AND TRADEMARK OFFICE
CERTIFICATE OF CORRECTION

| | | |
|---|---|---|
| PATENT NO. | : 7,892,254 B2 | |
| APPLICATION NO. | : 10/813783 | |
| DATED | : February 22, 2011 | |
| INVENTOR(S) | : Henrik S. Klint | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 407 days.

Signed and Sealed this
Twenty-eighth Day of June, 2011

David J. Kappos
*Director of the United States Patent and Trademark Office*